United States Patent [19]

Sherlock

[11] 4,192,295
[45] Mar. 11, 1980

[54] BEDSIDE DRAINAGE BAG

[75] Inventor: Hugh P. Sherlock, Palo Alto, Calif.

[73] Assignee: M.U. Engineering & Mfg. Co., Mountain View, Calif.

[21] Appl. No.: 792,971

[22] Filed: May 2, 1977

[51] Int. Cl.² ............................................... A61F 5/46
[52] U.S. Cl. .................................. 128/295; 128/275; 4/144.1
[58] Field of Search ...................... 128/295, 272, 275

[56] References Cited

U.S. PATENT DOCUMENTS

| 3,478,743 | 11/1969 | Ericson | 128/275 |
|---|---|---|---|
| 3,529,599 | 9/1970 | Folkman | 128/275 |
| 3,537,455 | 11/1970 | Skyles | 128/275 |
| 3,564,620 | 2/1971 | Clark | 4/110 |
| 3,568,965 | 5/1971 | Clark | 248/95 |
| 3,575,170 | 4/1971 | Clark | 128/275 |
| 3,661,153 | 5/1972 | Polk | 128/275 |

FOREIGN PATENT DOCUMENTS 2329088 1/1975 Fed. Rep. of Germany ............ 128/275
2,601,180 7/1976 Fed. Rep. of Germany ............ 128/275

Primary Examiner—Robert W. Michell
Assistant Examiner—Milford Juten
Attorney, Agent, or Firm—Flehr, Hohbach, Test

[57] ABSTRACT

A urinary drainage bag incorporating a handle, inlet and outlet tubes, and a vent is formed from two sheets of flexible plastic material joined together along their peripheries. The arrangement of parts is such that assembly is accomplished using a two-cycle sealing operation which can be done at one or a plurality of sealing stations. An inlet tube section and an outlet tube portion are disposed between the upper and lower margins of the sheets and are in axial alignment. Steps in the preferred method of manufacture include positioning the inlet tube section, a portion of the outlet tube, and the handle on a common mandrel prior to sealing. This assembly is then placed between the sheets and a sealing operation performed to produce all required seals. A segment of the seal is shaped to provide a labyrinth passageway vent.

9 Claims, 4 Drawing Figures

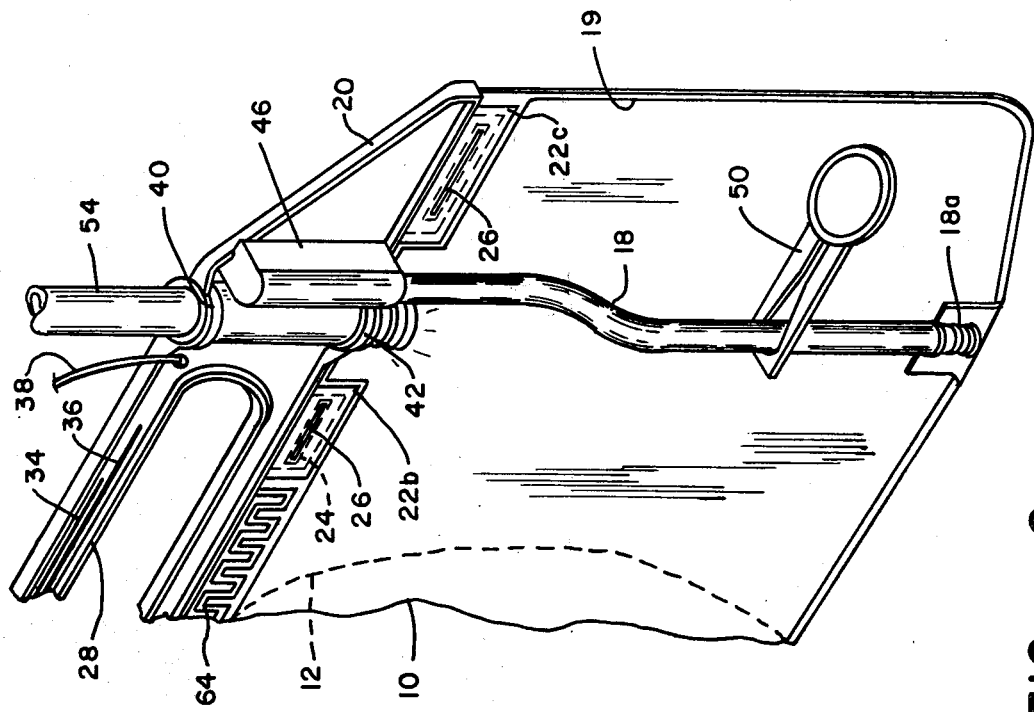
FIG.—2
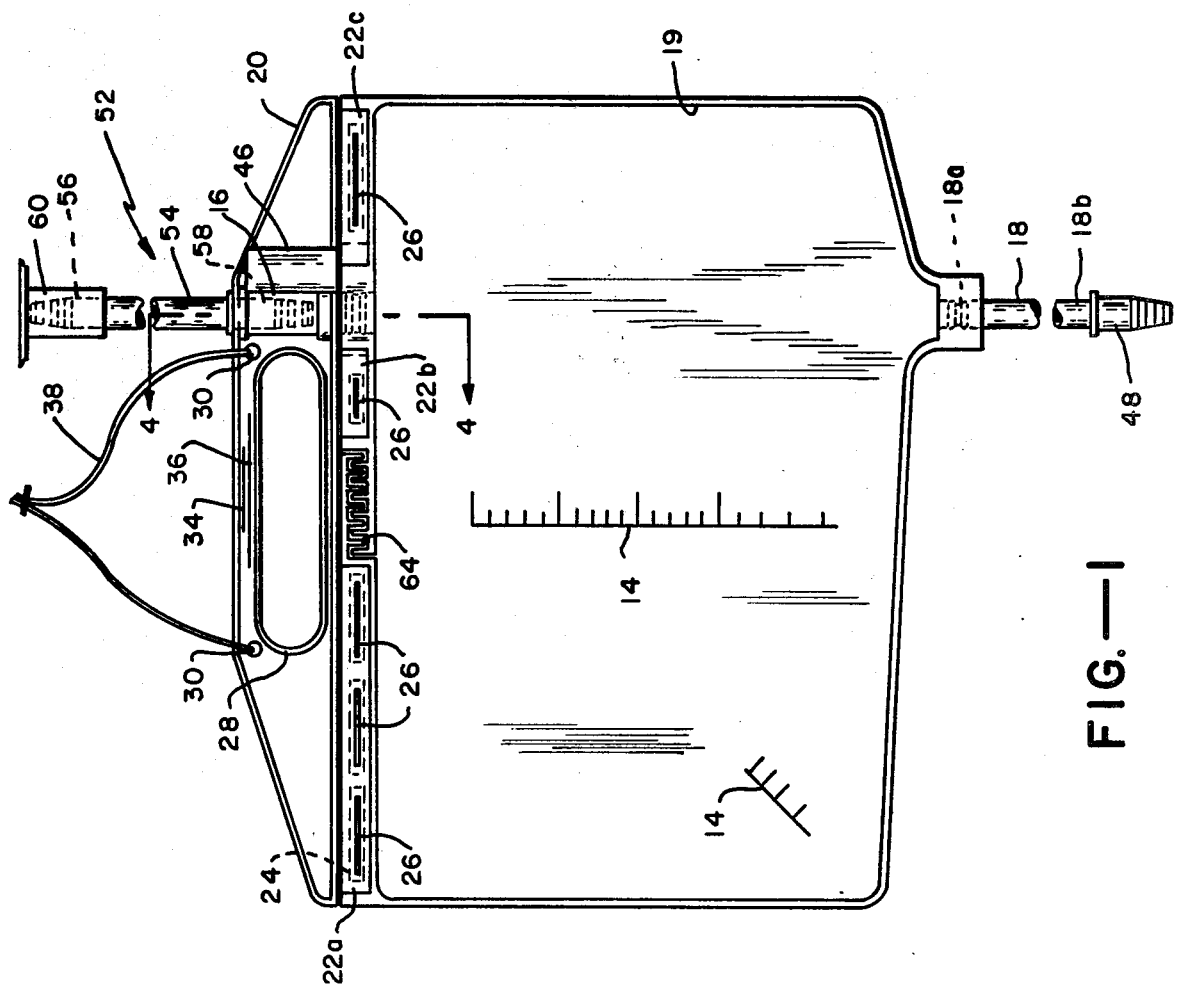
FIG.—1

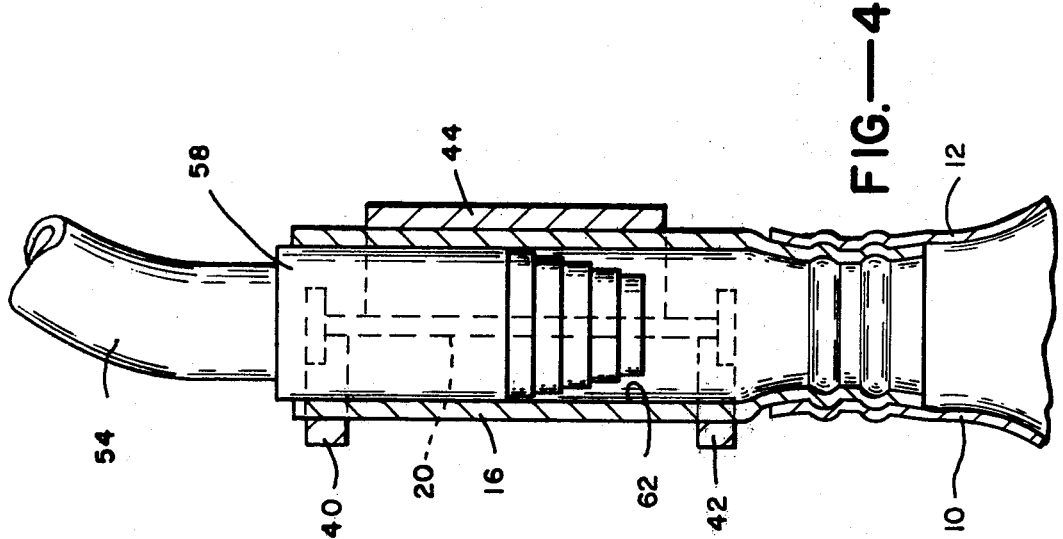
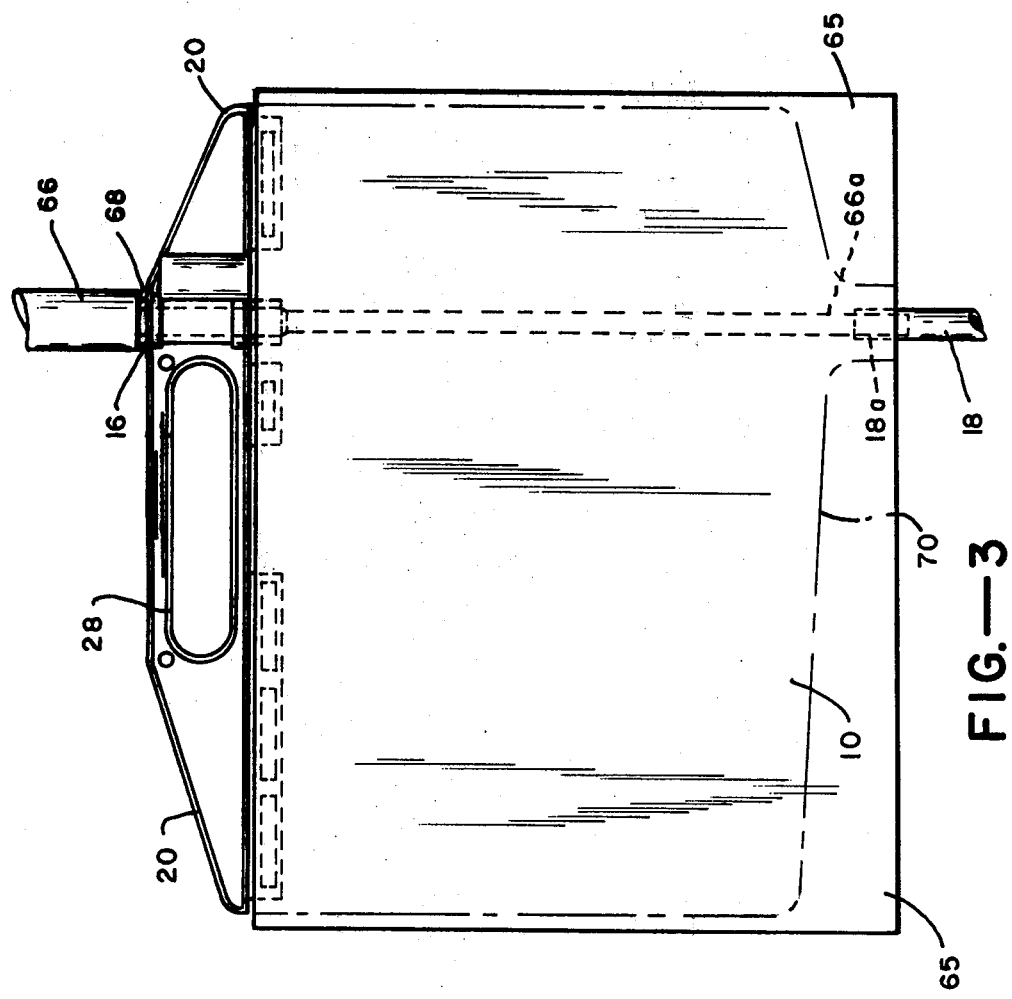

BEDSIDE DRAINAGE BAG

BACKGROUND OF THE INVENTION

This invention relates generally to urinary drainage bags and particularly to a method of manufacturing such bags.

Urinary drainage bags adapted for either bedside or portable use must function effectively while protecting the user from spills and infection. In general, such bags have inlet and outlet tubes communicating with an enclosed bag portion. They often include a handle or hanging means, and a retainer for storage of the loose outlet tube when not in use. Such a device is shown, for example, in U.S. Pat. No. 3,564,620, patented Feb. 23, 1971, by J. L. Clark.

Prior methods for making urinary drainage bags have employed a plurality of assembly and sealing operations. For example, at least one of the tubes and the handle are generally separately attached. The sheets of material from which the bags are formed are generally punched with holes for receiving the tubes, and each tube is separately sealed to the bag using a separate mandrel. These prior manufacturing methods are in part due to the structural features employed which do not lend themselves to simplified assembly.

OBJECTS AND SUMMARY OF INVENTION

In general, it is an object of the invention to provide an improved urinary drainage bag which is economical to manufacture.

Another object of the invention is to provide a method of manufacture using a single mandrel assembly.

Another object of the invention is to provide a method of manufacture employing a single two-cycle sealing operation.

The foregoing and other objects are achieved in a urinary drainage bag having side walls formed of sheets of flexible material. Inlet and outlet tubes are disposed coaxially between the upper and lower margins of the sheets with a seal extending along substantially the entire periphery of the sheets. A handle is attached to the top edge of the bag. The method of manufacture includes using a mandrel assembly in which the inlet and outlet tubes are placed on a common mandrel. In the preferred embodiment, a handle is also placed on the mandrel assembly which is then placed between the two flexible sheets. In a single two-cycle sealing operation the peripheral margins of the sheets are sealed together and also over the inlet and outlet tubes. Part of the seal also can engage a portion of the handle, attaching it to the bag. Preferably, non-uniform pressure is applied to seal the tubes between the sheets creating tapered seals which are less apt to fail.

Additional objects and features of the invention will be evident from the following detailed description taken in conjunction with the accompanying drawings.

BRIEF DESCRIPTION OF THE DRAWINGS

FIG. 1 is a side elevation view of a urinary drainage bag according to the invention in which the connecting inlet line and outlet tube are fragmented.

FIG. 2 is a fragmentary perspective view of the bag of FIG. 1 in which the outlet tube is folded against the bag when not in use.

FIG. 3 is a side elevation view of a mandrel assembly with the inlet and outlet tubes and handle on a mandrel positioned between the flexible sheets.

FIG. 4 is a sectional view along line 4—4 of FIG. 1.

DESCRIPTION OF THE PREFERRED EMBODIMENT

Referring to FIGS. 1 and 2, a urinary drainage bag according to the invention has side walls formed of sheets 10, 12 of flexible material such as polyvinylchloride or another suitable plastic. As illustrated, one such sheet 10 is formed of a clear or transparent material imprinted with volume markings 14 to allow the volume of liquid to be visually monitored.

A relatively short section of inlet tubing 16 is provided at the top of the bag. This inlet tube section 16 is sealed between the upper margins of the sheets 10, 12.

An outlet tube 18 is provided at the bottom of the bag, portion 18a of which extends between the sheets 10, 12. This outlet tube portion 18a is sealed between the lower margins of the flexible sheets 10, 12.

As shown in FIG. 1, outlet tube portion 18a is coaxial with inlet tube section 16. As will be described in detail below, this coaxial alignment facilitates the preferred method of manufacture in that it permits the tubes to be sealed using a common mandrel.

Sheets 10, 12 are bonded together to form a seal 19 between their margins. The seal extends along substantially the entire periphery of the sheets and also extends about inlet tube section 16 at 21 and about outlet tube end portion 18a at 23, forming a closed bag having openings for the passage of liquid only by way of the inlet tube section and outlet tube portion.

The portions 21 and 23 of peripheral seal 19 which are formed about inlet tube section 16 and outlet tube portion 18a are preferably tapered. This is done to accommodate the variations in tubing diameter encountered. Tubing which is substantially uniform will often vary in outside diameter within manufacturing tolerances. Such variations affect the pressure exerted on the seal when it is being formed. Since incorrect pressure can result in seal failure, it is desirable to apply pressure during sealing which is nonuniform along the length of tubing which is sealed between the sheets. Such a pressure gradient assures that the sealing pressure will be correct at least at some point along the seal. It also causes the resultant seal to be tapered, as shown at 21 and 23 of FIG. 1. More pressure is applied at the midpoint of the seal than at the ends, resulting in an hourglass shape. The ridges provide additional strength.

A handle 20 is provided along the upper edge of the bag. The preferred handle is fabricated of a substantially rigid material and has depending portions 22a–c. As illustrated, depending portions 22a–c include a plurality of rectangular openings 24. Handle 20 is retained on the bag by portions of the upper margins of sheets 10, 12 being bonded together to interlock with depending portions 22a–c. This interlock results from bonded portions 26 being within openings 24.

Handle 20 includes an opening 28 to accommodate the fingers of a hand grasping the handle to carry the bag. The handle also includes holes 30, 30 and slots 34, 36 for receiving a cord 38 or straps (not shown) by which the bag can be hung from a support. The preferred handle also includes means for engaging and supporting inlet tube portion 16 in a substantially upright position when the bag is in use. Such means includes members 40, 42, 44 which surround the inlet tube.

Retainer means 46 is also carried by the handle for holding the unattached end 18b of outlet tube 18 when the outlet tube is not in use. Preferably, unattached end 18b of the outlet tube is provided with a fitting 48, and retainer 46 is adapted to engage and hold such a fitting.

Outlet tube 18 is of sufficient length to reach retainer 46. This permits storage of the outlet tube in a position folded adjacent the side of the bag when not in use, as illustrated in FIG. 2. Fitting 48 is simply inserted in retainer 46 and held thereby. This method of storage for the outlet tube prevents leakage and makes the bag more compact for carrying. Additional protection against leakage is provided by stopper clip 50, which is placed over the outlet tube during assembly. It is preferred that outlet tube 18 be formed of a single, integral piece of tubing material of sufficient length to permit unattached end 18b to reach retainer 46. This eliminates the need to add additional tubing onto the outlet tube to complete the bag.

An inlet line 52 is included for carrying liquid into inlet tube section 16. A tube 54 having a diameter generally smaller than inlet tube section 16, is provided with tapered fittings 56, 58 at each end. Upper fitting 56 is generally employed for insertion into a urinary catheter. To maintain cleanliness of fitting 56 and the inlet line, a removable cap 60 is provided. Fitting 58 has an outer diameter which substantially conforms to the inner dimension of inlet tube section 16 and is preferably permanently installed therein with adhesive or the like.

As shown most clearly in FIG. 4, tapered fitting 58 disposed in inlet tube section 16 provides a path for liquid of a diameter less than the inner diameter of the inlet tube section. Thus, liquid moving down through the fitting will pass into the inlet tube section and bag without touching and wetting the interior surface of the tube indicated generally at 62. Surface 62 thus forms an annular portion of the interior surface of inlet tube section 16 which remains dry when the bag is in use. Such a dry annular surface inhibits bacterial movement from the bag up into the inlet line and thus serves to prevent user infection.

To provide gaseous ventilation for the bag, a portion of peripheral seal 19 located between the upper margins of sheets 10, 12 is made in the form of a labyrinth passageway 64 between the interior and exterior of the bag. Vent 64 is preferably in the form of a narrow unsealed portion following a generally zigzag path longitudinally along the upper margin between depending portions 22a and 22b of the handle. Such a pattern is known to inhibit the passage of bacteria. Other patterns are possible for the vent so long as it is generally formed to admit and expel air from the bag while preventing liquid from splashing or easily passing from the bag.

In use, the preferred urinary drainage bag may be hung by means of string 38 or straps passed through slots 34 and 36, or it may be carried. Until the bag is to be drained, outlet tube 18 is stored against the side of the bag as shown in FIG. 2, with fitting 48 held by retainer 46. To prevent any possibility of leakage, clip 50 may be moved generally leftward as seen in FIG. 2, to pinch and close the outlet tube. After protective cap 60 is removed, fitting 56 may be installed in a urinary catheter of the user. Liquid drains through inlet line 52 and into fitting 58 where it passes into inlet tube section 16 and the bag. Since the handle serves to maintain inlet tube 16 generally upright, annular portion 62 of the interior of inlet tube section 16 remains dry, preventing infection as described above. To drain the bag, the outlet tube is freed from retainer 46, clip 50 is shifted, and the liquid is permitted to drain from the bag, which is continuously vented by vent 64. The liquid level may be continuously monitored by means of volume markings 14.

From the foregoing, it may be seen that a preferred urinary drainage bag according to the invention has a number of safety and convenience features, and yet is of a form which lends itself to simplified manufacture. What follows is the preferred method by which this urinary drainage bag is made.

The two sheets 10, 12 of flexible material are first cut to size and may be imprinted with suitable markings 14 to indicate volume or the like. Preferably, the sheets are cut slightly oversize, having a generally rectangular shape as shown in FIG. 3 to permit easier handling and alignment. Final trimming of excess sheet material 65 is accomplished after the peripheral seal has been formed, as described below.

Inlet tube section 16 and outlet tube 18 are sealed between the sheets using a mandrel assembly. As shown in FIG. 3, the mandrel assembly comprises a single substantially straight mandrel 66 which is stepped to accommodate various tubing sizes. To form the mandrel assembly, the relatively short length of inlet tubing is first placed on the mandrel and moved into alignment with positioning means, such as shoulder 68 shown in FIG. 2. In making the preferred bag, handle 20 may then be placed over the inlet tube section, with members 40, 42, and 44 surrounding and engaging tube 16. To complete the mandrel assembly, end portion 18a of the outlet tube is placed on the end 66a of the mandrel spaced apart from the inlet tube. At this point the mandrel assembly holds all the elements which are to be sealed between the sheets, and these elements are positioned in their final mutual orientations.

The mandrel assembly is then positioned between the sheets. It is most convenient to spread lower sheet 12 on the lower portion of a die which is later used in the sealing operation. It is aligned using positioning means on the die. The mandrel is then lowered onto the lower sheet and upper sheet 10 is placed over it. FIG. 3 illustrates the parts thus arranged, before the sheets have been sealed. Means for positioning the parts quickly and efficiently might include, for example, mandrel 66 being hinged to the lower portion of the die. With the sheets properly positioned, a hinged mandrel would aid in maintaining proper mutual alignment of the parts during sealing. A number of lower die holders could be placed on a circular indexing type work table to permit shifting of the assembled parts for sealing.

Once the mandrel has been positioned between the sheets as shown in FIG. 3, with the inlet tube section and depending portions 22a-c disposed between the upper margins of the sheets, and outlet tube portion 18a disposed between the lower margins of the sheets, and with the edges of the sheets in opposition, the sealing step is performed. Numerous means are available to perform the sealing step. Such means might include, for example, sealing the sheets together with an adhesive or other bonding material. The preferred embodiment of the urinary drainage bag uses sheets made of thermoplastic material, such as polyvinylchloride. Sheets of such material can be sealed together by means of heat accompanied by pressure, as provided by the preferred sealing means described below.

In the preferred method, sealing is accomplished by means for directing electromagnetic energy to the margins of the sheets. A radio frequency sealer is employed using techniques known to those skilled in the art. When using such a sealer, an upper portion of the die is positioned over the assembled sheets and mandrel which rest on the lower portion of the die described above. One half of the die is then grounded and the other energized to direct electromagnetic energy to the margins of the sheets. To complete the seals around the tubes positioned on the mandrel it is then necessary to have a second cycle in which the mandrel is energized with the upper and lower die portions forming a common ground. This two-cycle sealing operation can be effected using automatic switching and the resultant seals are formed substantially contemporaneously. Alternative sealing cycles may be employed in the sealing operation. One such alternative would be to energize one die half and the mandrel in one cycle and the other half of the die in the second cycle. This would result in double sealing of the peripheral margin just as one half of each tube is double-sealed in the first-mentioned cycle, but this can be done without damaging results.

An alternative means for sealing the sheets together would employ a plurality of separate sealing stations. If a radio frequency sealer is used, each step of the two-cycle operation would be performed at a separate station. With the seals partially formed the mandrel assembly would be shifted to a second station having a second upper die portion to complete the seals. A plurality of such sealing stations could be used, if desired. Although the bag and assembly method are adapted for use with a single two-cycle sealing operation, the invention is not limited to such a sealing method.

During sealing, the margins of the sheets are sealed to each other along substantially the entire peripheries of the sheets. Seals are also formed about inlet tube section 16 and outlet tube portion 18a by applying pressure which is nonuniform along the length of tubing sealed. This forms a tapered seal which serves to protect against seal failure, as described above. The upper margins of the sheets are also bonded together at 26, within openings 24, to interlock with depending portions 22a–c and attach handle 20 to the bag. Also, seal 19 between the sheets along the upper margins is caused to form a labyrinth passageway 64 between the interior and exterior of the bag to provide gaseous ventilation for the bag as described above.

Use of the mandrel assembly shown in FIG. 3 also serves to simplify the method of manufacture. The coaxial alignment of inlet and outlet tubes permits use of a single mandrel for both tubes as well as aiding in its withdrawal.

Post-sealing steps in completing the bag include withdrawing the mandrel from the inlet tube section and the outlet tube portion. Removal of excess sheet material 65 is relatively simple because seal 19 creates an edge 70 along which to tear the sheet material. String 38 or hanging straps may be attached to the handle, and stopper clip 50 is installed. In addition, inlet line 52 is attached to inlet tube section 16 to provide the bacterial protection described above. This is done by inserting tapered fitting 58 into inlet tube section 16 to provide a path for liquid of reduced diameter. Fitting 58 may be permanently installed in the inlet tube as described above, using a solvent such a cyclohexanone. Similarly, fitting 48 is permanently installed to unattached end 18b of the outlet tube.

A urinary drainage bag has thus been described having important safety and convenience features, but which is economical to manufacture. Moreover, manufacture of the bag can be accomplished with only a single two-cycle sealing operation. It should nevertheless be understood that while a particular embodiment of a urinary drainage bag and method of manufacture have been described, various modifications and changes may be made within the scope of this invention, as set forth in the appended claims.

What is claimed is:

1. In a urinary drainage bag, first and second sheets of flexible material having upper, side and lower margins, and being disposed to form adjacent side walls of the bag, an inlet tube having a portion disposed between said upper margins of said first and second sheets, said inlet tube portion being offset from the center of said upper margins and adjacent one of said side margins of said first and second sheets, an outlet tube having one end portion thereof disposed between the lower margins and adjacent said one of said side margins of said first and second sheets and in alignment with said inlet tube portion, a peripheral seal bonding said sheets together along substantially their entire peripheries and also bonding said sheets about said inlet tube portion and said outlet tube portion to form a closed bag within said peripheral seal, said bag having openings for the passage of liquid only by way of said inlet tube and said outlet tube said bag having formed in the upper margin of the first and second sheets a labyrinth passageway which establishes a passage for the entrance of air into the bag while inhibiting the passage of bacteria, said labyrinth passageway being generally centrally disposed from the side margins of the first and second sheets, and a handle member formed of substantially rigid material having depending portions which extend between the upper margins of said first and second sheets outside said peripheral seal, said handle member being attached to said bag by portions of said sheets bonded to each other in a pattern which interlocks with said depending portions of said handle, said handle member having an opening therein disposed substantially equidistant from said side margins of said sheets to permit insertion of a hand to facilitate carrying of the bag.

2. A urinary drainage bag as in claim 1 wherein said inlet tube extends above said upper margins of said sheets and said handle member includes an open ended cylindrical portion for receiving and supporting a portion of said inlet tube extending above said upper margins in a substantially upright position when said bag is in use, said cylindrical portion being disposed adjacent one end of said handle member.

3. A urinary drainage bag as in claim 2 wherein said handle member includes an additional cylindrical portion having one end closed and a downwardly facing open end adjacent said one end of said handle member for receiving and retaining therein the other end portion of said outlet tube.

4. A urinary drainage bag as in claim 1 wherein a portion of said peripheral seal between the upper margins of said sheets defines a labyrinth passageway between the interior and exterior of said bag to provide gaseous ventilation for said bag.

5. A urinary drainage bag as in claim 1 together with an inlet line for carrying liquid and a tapered fitting carried by one end of said inlet line, said tapered fitting being disposed in said inlet tube and having a portion tapering away from said inlet tube whereby an annular portion of the interior surface of said inlet tube section remains dry when said bag is in use to inhibit bacterial movement from within the bag into the inlet line.

6. A urinary drainage bag as in claim 1 wherein the portions of said peripheral seal bonding said sheets about said inlet tube section and said outlet tube portion are tapered by application of pressure during formation of said peripheral seal which is non-uniform along the length of tube sealed between said sheets.

7. In a urinary drainage bag for use by a patient, first and second sheets of flexible material having upper, side and lower margins, and forming adjacent side walls of said bag an inlet tube having a portion disposed between the upper margins of said sheets and adjacent one of the side margins of the sheets, an outlet tube having a portion thereof disposed between the lower margins of said sheets adjacent said one side margins of the sheets and in alignment with said portion of said inlet tube, said outlet tube having an unattached end portion, a peripheral seal bonding said first and second sheets together adjacent their outer perimeters and also bonding said sheets about said portion of said inlet tube and said portion of said outlet tube to form a closed bag within said peripheral seal, said bag having openings for the passage of liquid only by way of said inlet tube and said outlet tube, a portion of said peripheral seal between the upper margins of said sheets defining a labyrinth passageway between the interior and exterior of said bag to provide an air vent for said bag while inhibiting the passage of bacteria, said labyrinth passageway being disposed between the upper margins of the first and second sheets and generally equidistant from the side margins of the first and second sheets and a handle member formed of a substantially rigid material having depending portions which extend between the upper margins of said sheets outside said peripheral seal, said handle member being attached to said bag by portions of said sheets bonded to each other in a pattern which interlocks with said depending portions of said handle member, said handle member having an opening therein disposed substantially equidistant from the side margins of said bag to permit insertion of a hand to facilitate carrying of the bag.

8. A urinary drainage bag as in claim 7 including an inlet line adapted to be connected to the patient for carrying liquid to said inlet tube and a tapered fitting carried by one end of said inlet line, said tapered fitting being disposed in said inlet tube and tapering away from said inlet tube so that an annular portion of the interior surface of said inlet tube section remains dry when said bag is in use to inhibit the passage of bacteria from the interior of the bag into the inlet line.

9. A urinary drainage bag as in claim 7 wherein the portion of said peripheral seal bonding said sheets about said inlet tube section and said outlet tube portion are tapered by application of pressure during formation of said peripheral seal which is non-uniform along the length of tube sealed between said sheets.

* * * * *